US00PP09038P

United States Patent [19]

Marciel et al.

[11] Patent Number: Plant 9,038

[45] Date of Patent: Jan. 10, 1995

[54] HYBRID TEA ROSE PLANT NAMED DEVCICO

[75] Inventors: Stanley G. Marciel; Jeanne A. Marciel, both of Aptos, Calif.

[73] Assignee: DeVor Nurseries, Inc., Freedom, Calif.

[21] Appl. No.: 185,708

[22] Filed: Jan. 24, 1994

[51] Int. Cl.[6] ..... A01H 5/00

[52] U.S. Cl. ..... Plt./18

[58] Field of Search ..... Plt. 11, 18

*Primary Examiner*—Howard J. Locker

*Attorney, Agent, or Firm*—Christie, Parker & Hale

[57] ABSTRACT

A new hybrid tea rose plant producing pink flowers.

1 Drawing Sheet

SUMMARY OF THE INVENTION

The present invention relates to a new and distinct variety of rose plant of the hybrid tea rose class which was originated by crossing as seed parent the variety known as 'Dolores' and as pollen parent the variety known as 'Cerise Dawn'. The varietal denomination of this new rose is 'Devcico'.

Among the novel characteristics possessed by this new variety which distinguish it from its parents and all other varieties of which I am aware are its attractive pink flowers having a classic balled center.

Asexual reproduction by budding of the new variety as performed in Watsonville, Calif. shows that the foregoing and other distinguishing characteristics come true to form and are established and transmitted through succeeding propagations.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—'Dolores'.

*Pollen parent.*—'Cerise Dawn'.

Class: Hybrid tea.

The following is a detailed description of my new variety, of new specimens grown under glass in Watsonville, Calif. in the month of September. The color terminology used is in accordance with the Royal Horticultural Society Colour Chart (RHSCC), and refers to plate numbers in the aforementioned color chart. Phenotypic expression may vary depending on light, environmental and cultural conditions.

FLOWER

Blooming habit: Continuous.

A. Bud:

(1) *Size.*—Medium.

(2) *Form.*—Pointed bud.

(3) *Color.*—Before sepals divide, near 47D.

(4) *Sepals.*—Spreading with some pointed leaf ends, upright and close to bud and somewhat foliaceous; about $\frac{3}{4}$ to $\frac{7}{8}$ size of bud.

(5) *Peduncle.*—Length: About 9–13.5 cm. Aspect: Straight, small prickles. Strength: Erect, sturdy. Color: Near 144A.

(6) *Bracts.*—None.

B. Bloom:

(1) *Size.*—Average size when fully expanded — about 12 cm.

(2) *Borne.*—Singly, one to a stem.

(3) *Form.*—Imbricated, high-centered at first.

(4) *Petalage.*—Number of petals under normal conditions — about 19–21.

(5) *Color.*—$\frac{1}{3}$ to $\frac{1}{2}$ open: Top surface of outer petals is near 54C at top, with center near 49A and base near 10D; undersurface of outer petals is near 55D at top, with center near 55C and base near 50D; top surface of inner petals is near 50C at top, with center near 52D and base near 48D; undersurface of inner petals is near 54C at top, with center near 54C and base near 51D; color at base of petals (point of attachment) is near 1B and the general tonality from a distance is pink. Fully open blooms: top surface of outer petals is near 52D at top, with center near 52D and base near 8D; undersurface of outer petals is near 55C at top, with center near 55C and base near 55D; top surface of inner petals is near 49A at top, with center near 49A and base near 49B; undersurface of inner petals is near 54C at top, with center near 48C and base near 49C; color at base of petals (point of attachment) is near 1C and the general tonality from a distance is pink. Color of bloom upon aging lightens to a light white pink, with the petal top surface near 55D and the petal undersurface near 56A, and the general tonality at a distance is light pink.

C. Petals:

(1) *Texture.*—Thick, soft, smooth.

(2) *Appearance.*—Inside semi-velvety and outside matte.

(3) *Form.*—Curled.

(4) *Arrangement.*—Regularly arranged, imbricated but with balled center.

(5) *Petaloids.*—Few.

(6) *Fragrance.*—Sweet.

(7) *Lasting quality.*—7–10 days as cut flower; petals hold well for greenhouse variety.

REPRODUCTIVE ORGANS

A. Stamens:

(1) *Arrangement.*—Regularly arranged.

(2) *Anthers.*—Color near 26B.
(3) *Filaments.*—Near 1C, middle near 51C, top near 155B.
(4) *Pollen.*—Color near 27B.

B. Pistils:
(1) *Styles.*—Bunched, uneven length.
(2) *Stigmas.*—Color near 27B.

C. Characteristics of hips: Not observed.

PLANT

A. Form: Upright.
B. Growth: Vigorous, uniform branching.
C. Foliage: Compound 3, 5 and 7 leaflets.
(1) *Size.*—Large.
(2) *Quantity.*—Abundant.
(3) *Color.*—New foliage — upper side near 147A, underside near 147B; old foliage — upper side near 137A, underside near 137C.
(4) *Shape.*—Mucronate.
(5) *Texture.*—Leathery, semi-glossy.
(6) *Edge.*—Serrate.
(7) *Serration.*—Denticulate.
(8) *Leaf stem.*—Color — medium green.
(9) *Stipules.*—Narrow, long, smooth.
(10) *Rachis.*—Smooth.

(11) *Petioles.*—Top near 146B, underside near 146D.
(12) *Auricle.*—Very long, pointed outward.
(13) *Resistance to disease.*—Under greenhouse conditions no rust and blackspot; good resistance to mildew.

D. Wood:
(1) *New wood.*—Near 146B, smooth.
(2) *Old wood.*—Color near 146A, smooth.

E. Flower Stem: About 55–59 cm from last cut.

F. Thorns:
(1) *Thorns.*—Quantity: On main stalk, few; on laterals from stalk, few. Form: Some curved downward, small. Length: Short. Color: Near 181D when young. Position: Irregular.
(2) *Prickles.*—Some.

F. Winter hardiness: Greenhouse variety; wintered well in California, good bloomer in greenhouse under winter conditions.

I claim:

1. A new and distinct variety of rose plant of the hybrid tea rose class, substantially as shown and described.

* * * * *

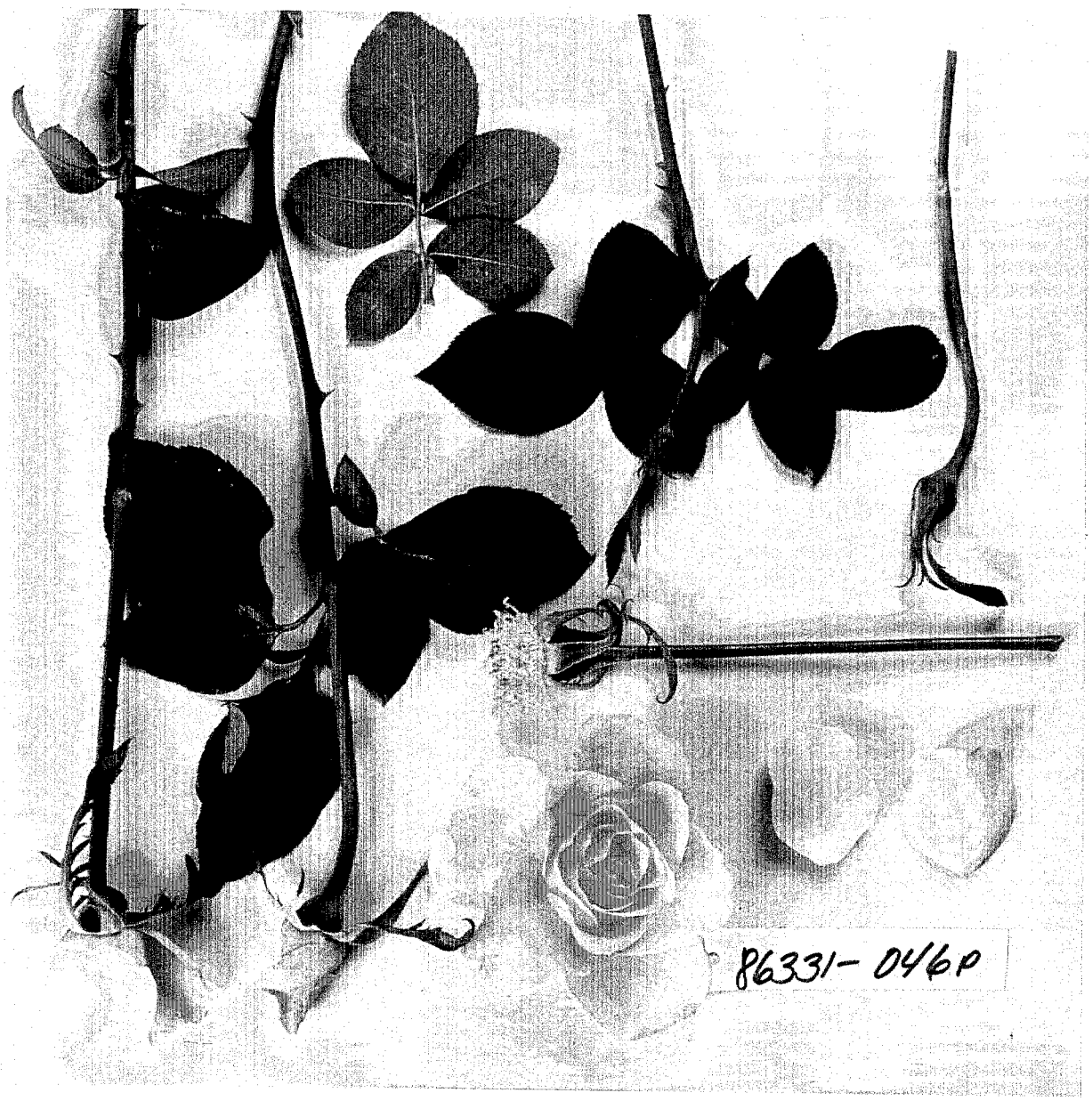
86331-046P